United States Patent [19]

McGarrity et al.

[11] Patent Number: 5,372,942
[45] Date of Patent: Dec. 13, 1994

[54] PROTEASE K RESISTANT ARGININE DEIMINASE, ITS METHOD OF PREPARATION AND ITS USE AS AN ANTI-NEOPLASTIC AGENT

[75] Inventors: Gerard J. McGarrity, Wenonah; Gary H. Butler, Cherry Hill, both of N.J.

[73] Assignee: Coriell Institute for Medical Research, Camden, N.J.

[21] Appl. No.: 198,375

[22] Filed: Feb. 18, 1994

Related U.S. Application Data

[63] Continuation of Ser. No. 833,142, Feb. 10, 1992, abandoned.

[51] Int. Cl.$^5$ .................. C12N 9/78; C07K 15/04
[52] U.S. Cl. ........................ 435/227; 435/815; 530/416
[58] Field of Search ............ 435/227, 815; 530/416

[56] References Cited

PUBLICATIONS

Butler et al. (Mar. 1991) *Infect. Immun.* 59(3), 1037–1042.
Schimke et al. (1966), *J. Biol. Chem.*, 24(10), 2228–2236.
Weickmann et al. (1977), *J. Biol. Chem.* 252(8), 2615–2620.
Kondo et al. (1990) *MGG. Mol. Gen. Genet.*, 221, 81–86.
Sugimura et al. (Aug. 1990) *Infect. Immun.*, 58(8), 2510–2515.
Ohno et al. (Nov. 1990) *Infect. Immun.*, 58(11), 3788–3795.
Takaku et al. (1992) *Int. J. Cancer*, 51(2), 244–249.
Miyazaki et al. (Aug. 1990) *Cancer Res.*, 50, 4522–4527.
Nakamura et al. (1983) *Curr. Microbiol.* 9(4), 177–185 in *Chem Abst.* 100(9), 295, Abst #64584.
Itoh et al. (1984) *Kurume Igakkai Zasshi*, 47(10), 1183–1187, in *Chem. Abstr.*, 102(23), 329, Abst. #200,813.
Sato et al. (5 Feb. 1990) JP 02035081, in *Chem. Abstr.*, 113(25), 317, Abst. #227,136.
Horyo et al., (22 Feb. 1990) JP 02053490, in *Chem. Abst.*, 113(19), 222, Abst. #166,908.
Takaku et al. (27 Feb. 91) EP 414,007, in *Chem Abst*, 115(1), 703, Abst. 190 7016.
Schimke (1970) in *Method Enzymol.*, XVII, pp. 310–313, Ed. Tabor et al., Acad. Press, New York.

*Primary Examiner*—Douglas W. Robinson
*Assistant Examiner*—Jon P. Weber
*Attorney, Agent, or Firm*—Banner, Birch, McKie and Beckett

[57] ABSTRACT

A highly purified arginine deiminase is obtained using a two-step purification procedure. The arginine deiminase is isolated and purified from various species of mycoplasmas and is resistant to proteinase K. The growth of tumor cells can be inhibited by administering proteinase K-resistant arginine deiminase or a PEG-conjugate thereof.

7 Claims, 8 Drawing Sheets

PROTEASE K RESISTANT ARGININE DEIMINASE, ITS METHOD OF PREPARATION AND ITS USE AS AN ANTI-NEOPLASTIC AGENT

This application is a continuation of application Ser. No. 07/833,142, filed Feb. 10, 1992, now abandoned.

FIELD OF THE INVENTION

The invention relates to an enzyme, arginine deiminase. In particular, it relates to a unique arginine deiminase isolated from mycoplasmas. More particularly, the invention is directed to a mycoplasmal proteinase K resistant arginine deiminase and to a method of preparing proteinase K resistant arginine deiminase in highly purified form. The invention further relates to a method of inhibiting the growth of tumor cells by administering mycoplasmal proteinase K resistant arginine deiminase, or a PEG-conjugate thereof, as an anti-neoplastic agent.

BACKGROUND OF THE INVENTION

Arginine deiminase is an enzyme which catalyzes the irreversible hydrolysis of arginine, an essential amino acid, to citrulline and ammonia. Arginine deiminase, a type of arginase, has been found in a number of species, both prokaryotic and eukaryotic. Arginases have been identified in liver cells, skin cells, bacteria such as streptococci, yeasts, and in various mycoplasmas. Some species of mycoplasmas use arginine deiminase as part of their energy generating metabolism and, as such, are good sources of this enzyme.

Mycoplasmas represent the simplest form of a self-replicating organism. They are small, bacteria-like microorganisms which, unlike bacteria and other prokaryotic cells, lack a cell wall. Their genome size, which is about $5 \times 10^8$ daltons, is approximately one sixth that of *Escherichia coli*. Mycoplasmas inhabit the alimentary, respiratory and genito-urinary tracts of humans and animals and are a common contaminant of cell cultures.

Two major pathways exist for the generation of energy in mycoplasmas. One is classical glycolysis, wherein glucose is broken down into pyruvic acid and ATP. The second is the utilization of arginine. In this second pathway, arginine deiminase converts arginine to citrulline, and ultimately to $NH_3$, $CO_2$ and ATP. This mechanism is illustrated below:

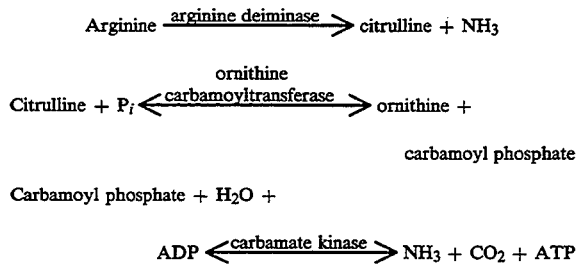

Mycoplasmas may be classified into arginine-positive or arginine-negative organisms. Most arginine-positive species do not ferment glucose and most fermenters do not hydrolyze arginine. Some, however, metabolize both. Barille (In: Methods in Mycoplasmology, Vol. 1, 1983, pp. 345–448).

Mycoplasmas which use arginine as an energy source (arginine positive), typically have large amounts of arginine deiminase in their cytoplasm. Schimke et al. (J. Biol. Chem. (1966) 241:2228–2236) found that the enzyme constitutes about 10% of the cytoplasmic protein of *Mycoplasma arthritidis*. As such, and as indicated above, mycoplasmas using arginine deiminase as part of their energy generating metabolism are good sources of enzyme.

Some species of mycoplasma are pathogenic to humans, the most notable being arginine-negative *M. pneumoniae*, which produces pneumonia. Other species of mycoplasma produce diseases in laboratory, farm and domestic animals, citrus plants and other crops, and in insects.

Two of three species from which arginine deiminase has been routinely prepared, *M. orale* and *M. salivarium*, are non-pathogenic, normal human flora. The third, *M. arginini* is a bovine isolate.

As mentioned above, mycoplasmas are common contaminants of cell culture. They produce a diversity of effects in cell culture including changes in viral titers, induction of interferon, mitogenesis, induction of cytokines, chromosomal aberrations, and activation of macrophages.

Mycoplasmal arginine deiminases are 1000 times more potent than mammalian arginases in inhibiting the growth of human tumor cells in vitro. Miyazaki et al. (Ca. Res. (1990) 50:4522–4527). Bach et al. (Br. J. Ca. (1965) 19:379–384). However, their development as anti-neoplastic agents and any unfavorable effects in vivo remain to be thoroughly explored.

Anti-neoplastic agents which inhibit the metabolism of rapidly proliferating cells has been the mainstay in cancer chemotherapy. Most chemotherapeutic drugs (e.g., methotrexate, cyclophosphamides) have adverse side effects and many (e.g., L-asparaginase) are limited in their effectiveness by high dose requirements and restricted responsive tumor types. Thus, the evaluation of new, and hopefully better cancer chemotherapeutics, especially for those which may be effective in lower doses is a priority.

Thousands of compounds have been evaluated for in vitro anticancer activity. Only a few, however, have become clinically useful. Among these is one amino acid depleting enzyme, L-asparaginase. L-asparaginase has had success as an anti-cancer drug, especially in conjunction with other drugs, and in the treatment of acute lymphoblastic leukemia (ALL) and late stage cancers. L-asparaginase depletes the cells of the non-essential amino acid asparagine. L-asparaginase is advantageous in that it has been found to be relatively non-toxic for bone marrow. L-asparaginase, however, exhibits side effects which include allergic reactions (including anaphylaxis), hyperglycemia, liver dysfunction, coagulopathy, pancreatitis and CNS dysfunction. Evans et al. (Cancer (1990) 65:2624–2630); Hudson et al. (Cancer (1990) 65::2615–2618); Asselin et al. (Ca. Res. (1989) 49:4363–4368).

Those side effects related to L-asparginase being an immunogen (immune response) and those related to reduced protein synthesis as a consequence of amino acid depletion (e.g., coagulopathy and liver dysfunction) may be reasonably expected for arginine deiminase since it shares these properties. However, it can be expected that the immune response to arginine deiminase may be greatly reduced as an adverse side effect because the in vitro potency of this enzyme predicts lower doses will be required and thus lower side effects. While arginine deiminases convert the essential amino acid arginine to citrulline, it has not yet been determined that arginine depletion is the mechanism of tumor cell killing. It does, however, remain a likely theory.

It is known in the art that the covalent attachment of polyethylene glycol (PEG) to a protein blocks attack by degradative enzymes thereby inhibiting clearance from the circulation and converts immunogenic substances to nonimmunogenic derivatives. Brueck et al. (Der. Pharmacal. Ther. (1989) 12:200–204); Savoca et al. (Cancer Biochem. Biophys. (1984) 7:261–268); Abuchowski et al. (J. Biol. Chem. (1977) 252:3578–3582 and Cancer Treat. Rep. (1979) 63:1127–1132). U.S. Pat. No. 4,002,531 discloses a method of preparing PEG derivatives of enzymes having greater stability and greater retention of enzyme activity. U.S. Pat. No. 4,179,337 discloses the coupling of PEG to various polypeptides such as enzymes and peptide hormones such as insulin. U.S. Pat. Nos. 4,777,106 and 4,917,888 disclose the conjugation of PEG to an immunotoxin, β-interferon and Interleukin 2. U.S. Pat. No. 4,791,192 discloses PEG-islet-activating protein (IAP) conjugates. The conjugates are described as having strong islet-activating activity and as producing less side effects than non-modified IAP. U.S. Pat. No. 4,847,325 discloses various methods of conjugating colony stimulating factor-1 (CSF-1) to PEG. The PEG-CSF-1 conjugate is described as being biologically active and as having an increased circulating half life. The conjugation of PEG to enzyme-type chemotherapeutics hold promise for an increased circulatory half-life and decreased immunogenicity of such chemotherapeutics.

Animal studies have suggested that arginase retard growth of some tumors in vivo. Bach et al. (Br. J. Ca. (1965) 9:379–384) demonstrated that bovine liver arginase inhibited the growth of Walker carcinoma cells in 31 of 40 (77%) rats for four days after the inoculation of tumor cells. However, survival time of animals was not significantly affected. Savoca et al. (Cancer Blochem. Biophys. (1984) 7:261–268) were able to both reduce tumor mass and extend the lives of rodents inoculated with tapir liver tumor cells and given bovine liver arginase modified with PEG to reduce immunogenicity and extend the circulating life of the enzyme. In these studies, 45% of the PEG-modified arginase remained in plasma after 24 hours, and 16% remained after 72 hours. In contrast, only 1% of non-modified arginase remained after 24 hours. The use of PEG-modified arginase was found to significantly increase survival of animals. Eighteen of 29 mice inoculated with tapir liver tumor cells survived greater than 60 days. Untreated animals survived a mean of 20 days. Fifteen of the 18 survivors were negative for gross or histological evidence of tumors.

Miyazaki et al. (Ca. Res. (1990) 50:4522–4527) identified tumor cell growth inhibitory activity in Rous sarcoma virus-transformed buffalo-rat liver (RSV-BRL) cells cultured in serum free conditioned media (SFCM) and discovered that the RSV-BRL cells were mycoplasma contaminated. It was determined that the growth inhibitory activity was due to mycoplasmal arginine deiminase. The enzyme was purified from the SFCM of the mycoplasma contaminated RSV-BRL cells and was shown to inhibit the growth of tumor cell lines in vitro. Although the species of the mycoplasmal contaminant was not identified, it was most likely one of the most common arginine deiminase producing tissue culture contaminants: *M. arginini*, *M. orale*, *M. salivarium* or *M. fermentans*. The enzyme and cytotoxic activity were absent after curing the cell culture of myeoplasmas. The arginine deiminase was effective against numerous human cancer cell lines including hepatomas, squamous cell carcinomas of the tongue and cervix, adenocarcinomas of the lung, nose and colon, glioblastoma, myeloma and melanoma. The mycoplasmal arginine deiminase was toxic for tumor cell lines at doses of 5 ng/ml. This was 1000-fold less than the previously reported minimal effective dose of bovine liver arginases.

The significantly increased specific activity of the mycoplasmal enzyme may be clinically advantageous. For example, lower doses may avoid serious immune reactions, such as anaphylaxis, which occur with the proteinaceous anti-neoplastic agent L-asparaginase. The extremely low in vitro effective dose of mycoplasmal arginine diaminase predicts lower in vivo doses and decreased risks of side effects.

The cloning and sequence analysis of arginine deiminase, but not expression of the protein, from one species of mycoplasma, *M. arginini*, has been reported by Ohno et al. (Infect. and Immun. (1990) 58:3788–3795) and Kondo et al. (Mol. Gen. Genet. (1990) 221:81–86).

SUMMARY OF THE INVENTION

The object of the invention is to provide a method of purifying a unique mycoplasmal arginine deiminase which is simpler than the prior art method. The mycoplasmal arginine deiminase is obtained in high yield directly from mycoplasmas, is selectively resistant to proteinase K and is obtained in highly pure form using a simple two-step process.

A further object of the invention is to provide antineoplastic agents which are safer and more effective at lower doses. The proteinase K resistant arginine deiminase is 100% toxic for tumor cells in vitro at 20 ng/ml and is not toxic for mice when administered intraperitoneally at 1 mg/ml.

DETAILED DESCRIPTION OF THE PREFERRED EMBODIMENTS

Figure 1:
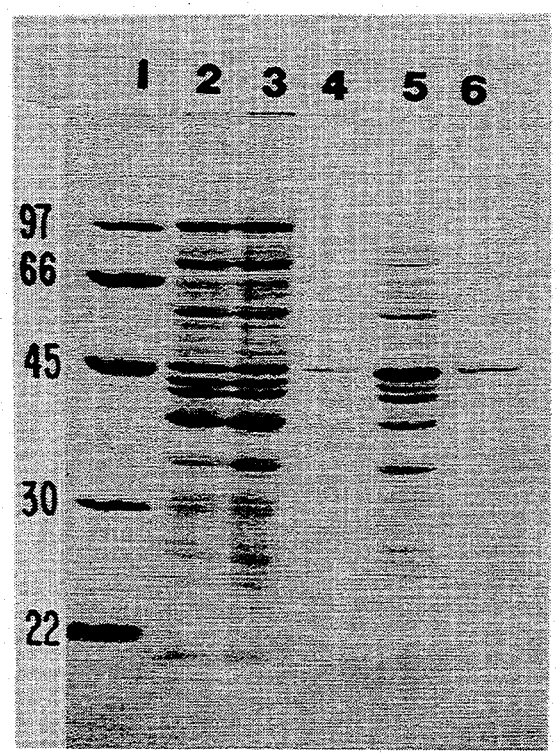
FIG. 1 compares proteinase K digest of water and CHAPS extracts of *M. orale*.

Whereas Miyazaki et al. (Ca. Res. (1990) 50:4522–4527) purified a potent tumor killing mycoplasmal arginine deiminase from SFCM, it has been discovered that a proteinase K-resistant form with equal potency can be purified directly from mycoplasmas in large quantities.

Purification of mycoplasmal arginine deiminase from a broth grown culture of mycoplasmas in large quantity, rather than in lower quantity from complex cell culture conditioned medium which may contain other tumor inhibitors, simplifies purification since contamination with eukaryotic-derived growth inhibitors is not a concern and the enzyme is much more concentrated. Mycoplasmal arginase deiminases purified from broth-grown *M. arginini* and *M. orale* were found to kill 100% tumor cells in vitro at 20 ng/ml, the minimum dose tested. This finding confirms the findings of Miyazaki et al. (Ca. Res. (1990) 50:4522-4527), which demonstrated 40-50% toxicity of a mycoplasmal enzyme for tumor cells at 5 ng/ml.

It has been further discovered that mycoplasmal arginine deiminases may be purified much more easily and in higher quantities directly from mycoplasmas. The absence of a slime layer and a cell wall in mycoplasmas, and their reduced genetic, structural and enzymatic complexity relative to bacteria makes the purification of arginine deiminases from them easier and reduces the possibility of contaminants such as endotoxins, which may produce unfavorable reactions in vivo.

Purification of arginine deiminase directly from organisms significantly enhances yields since it is a major component of most species possessing it. Arginine deiminase may comprise as much as 5-20% of the total protein in most species of mycoplasma having this enzyme. Razin (Micro. Rev. (1978) 42:414-470).

An even greater purification of a unique mycoplasmal arginine deiminase is now possible by the discovery that some forms of this enzyme are selectively and highly resistant to digestion by proteinase K.

Proteinase K is a serine protease derived from the mold *Tritirachium album* Limber. Ebeling et al. (Eur. J. Biochem. (1974) 47:91-97). Proteinase K hydrolyzes all peptide bonds adjacent to carboxyl ends of amino acids with blocked alpha amine groups, typically leaving only the bond joining the N-terminal dipeptide of the protein intact. Proteinase K is commonly used in the range of 5 to 500 $\mu$g/ml and digests most proteins completely in 5 minutes to 2 hours at 100 $\mu$g/ml.

The use of proteinase K in a method of purifying proteinase K resistant arginine deiminase serves to destroy minor protein components not easily detected by analytical methods, thereby reducing trace contamination of other proteins.

The method of purifying proteinase K resistant arginine deiminase according to the invention involves a simple two-step procedure comprising (1) digesting a detergent (e.g., Triton-X or CHAPS (3[3-cholamidopropyl]-dimethyl-ammonia)-2-propane-sulfonic acid]) extract or a water extract with proteinase K and (2) filtering and subjecting the filtrate to high pressure liquid chromatography (HPLC).

In the method according to the invention, the initial proteinase K digestion accomplishes the majority of purification from other proteins. Gel analysis of crude proteinase K digests generally shows only a single major band correlating to a $M_r$ of reduced arginine deiminase, i.e., $4.6 \times 10^4$ daltons. Proteinase K treatment of either CHAPS or water extracts gives approximate 30-fold purification (increase in specific activity) from other protein components as a single step. Since arginine deiminase is a major protein component of mycoplasmas to begin with, much higher fold purification has little significance. Subsequent filtration and HPLC purification steps remove proteinase K, digestion products, minor protein contaminants and non-protein contaminants.

The extraction protocol is optimized by sonification in water, which eliminates the need for removal of detergent by extensive dialysis. FIG. 1 is a comparative analysis of *M. orale* water and CHAPS extracts and proteinase K digests in 12.5% SDS-PAGE gels with Coomassie staining. Identical results are obtained with *M. arginini*. Lane 1—$M_r$ markers. Lane 2—SDS extract. Lane 3—water extract. Lane 4—proteinase K-digested water extract. Lane 5—CHAPS extract. Lane 6—proteinase K-digested CHAPS extract.

Preliminary culture and extraction procedures may be conducted as reported by Butler et al. (Infect. and Immun. (1991) 59:1037-1042).

Mycoplasmas are grown in standard mycoplasma broth medium containing 10% horse serum, with or without $10^3$ U/ml penicillin G, at 37° C. for 1 to 4 days aerobically or anaerobically as appropriate for each organism. Myeoplasmas are recovered by centrifugation at 12,000 $\times$ g and washed three times in phosphate-buffered saline.

Washed mycoplasma pellets are suspended in 25 mM CHAPS or water and disrupted with a Branson Sonifier conicator. The extraction is continued at 10° C. Supernatants of CHAPS extracts are dialyzed four times against 400 volumes of phosphate-buffered saline at 10° C. to remove the CHAPS. Supernatants of water extracts are not dialyzed. Insoluble material is removed by centrifugation at 100,000$\times$g for 2 hours. Protein content is determined using BCA reagent (Pierce, Rockford, Ill.). The extracts are then treated with proteinase K (Boehringer Mannheim, Indianapolis, Ind.), isolated and HPLC-purified.

In a preferred embodiment, the extraction procedure is optimized to maximize yield, minimize manipulation, reduce time, and eliminate the need for removal of detergent. In accordance with the preferred embodiment, mycoplasmas are recovered by centrifugation at 12,000$\times$g for 20 minutes at 4° C. and washed twice in 250 ml volumes of 0.25M NaCl, 0.02M sodium phosphate, pH 7.2. The hypertonicity of this wash buffer compensates for the high osmolality of the mycoplasma medium and inhibits lysis of cells by hypo-osmotic shock (Rottem In: Methods in Mycoplasmology, Vol. 1, 1983, pp. 221-223).

The washed mycoplasma pellets are then incubated in 5 ml of wash buffer containing 0.01M MgCl$_2$ and 25 $\mu$g/ml DNAse at 37° C. for 15 minutes prior to further washing. Subsequent proteinase K treatment will destroy residual DNAse.

The pellets are then suspended at approximately 100 mg wet weight pellet mass/ml of endotoxin-free water and mycoplasmas lysed by sonification at 4° C. with a Branson sonifier sonicator. Insoluble material is removed by centrifugation at 100,000$\times$g for one hour at 4° C. The supernatants are then adjusted to 0.1M sodium phosphate, pH 7.25, with or without $10^3$ U/ml penicillin G, and 20 $\mu$g proteinase K per ml of protein, and incubated at 37° C. with continuous shaking for 16 hours.

At this stage, arginine deiminase constitutes 90-100% of the remaining protein, however, non-protein contaminates remain. Proteinase K-digestion products and other small molecules can be removed with an Amicon 8010 10 ml nitrogen pressure concentrator with PM-30 kDa cutoff membrane. This apparatus is also used to accomplish volume reduction to 1-2 ml and buffer exchange to 0.02M Tris, pH 7.9 for subsequent HPLC purification. Samples can be either HPLC-purified immediately or frozen at $-70$° C. It has been observed that proteinase K resistant arginine deiminase is stable for approximately 10 months at $-70$° C. Longer periods are predicted following lyophilization of the enzyme.

It is noted that the proteinase K digestion conditions described above, including high phosphate concentration, are necessary to accomplish the selective resistance of arginine deiminases to proteinase K.

Generally 0.5–1.0 gm of weight wet organisms are obtained per liter yielding 0.5–5.0 mg arginine deiminase upon purification.

Cloning may increase efficiency and yields at least 10 fold, and probably more, if the enzyme can be expressed in bacteria as L-asparaginase has been.

EXAMPLE 1

Anion-exchange HPLC purification of proteinase K-resistant arginine deiminase was performed on analytical columns using Triton-X or CHAPS in phosphate or Hepes buffer system as described by Dj Josic et al. (J. Chromatog. (1986) 359:315–322). The arginine deiminases purified by these methods have specific activities of 40–60 μmole citrulline produced per mg of protein, similar to that reported by Schimke (Ann. N.Y. Acad. Sci. (1967) 143:573–577) and Schimke et al. (J. Biol. Chem. (1966) 241:2228–2236 and J. Bact. (1963) 86:195–206).

Figure 2:
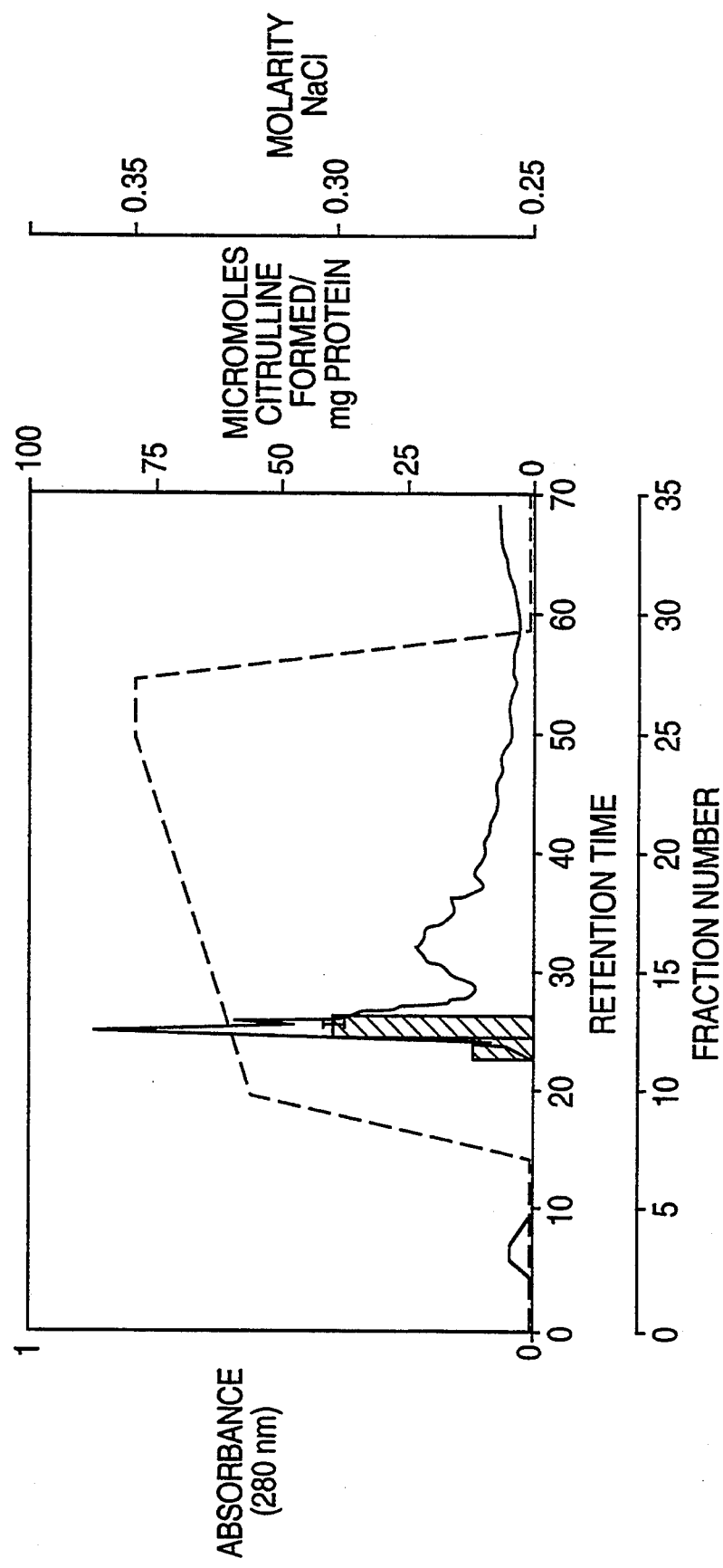
FIGS. 2, 3, and 4 shows the purification and identification of proteinase K resistant arginine deiminase.
Figure 3A:
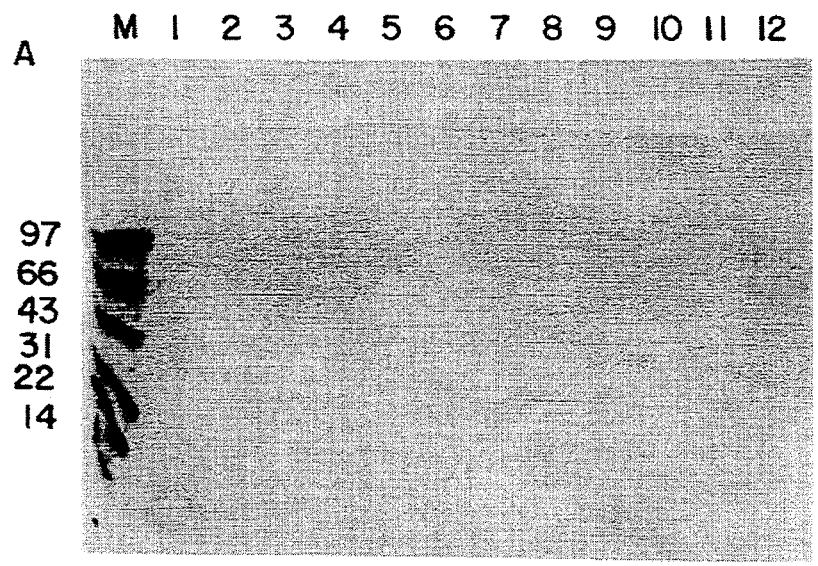
Figure 3B:
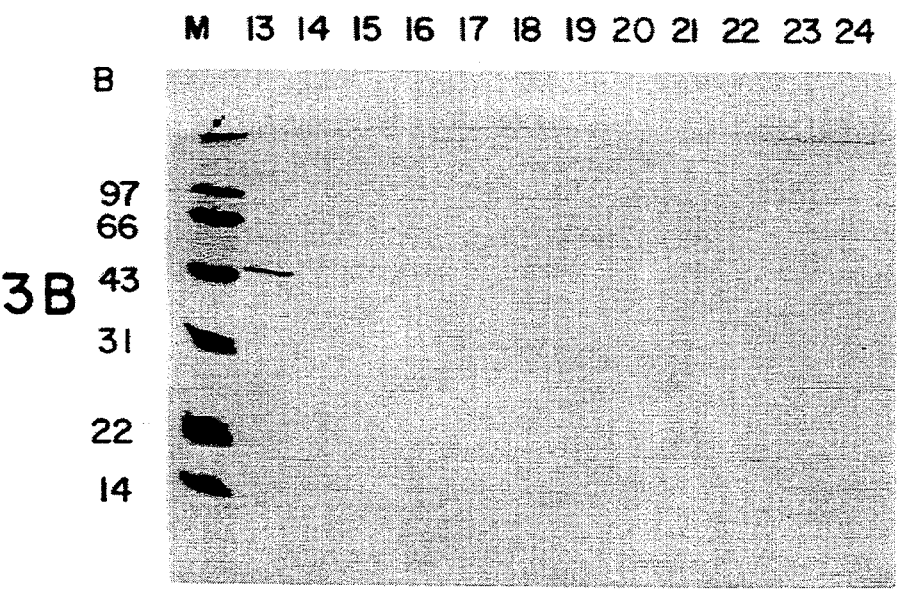

FIG. 2 shows the anion-exchange (analytical 0.75×75 mm Waters' DEAE 5PW column) HPLC purification of the 46,000 Mr proteinase K-resistant protein from M. orale with Triton X-100 in buffers, and identification of this protein as arginine deiminase. A complex linear gradient was run from 10 mM Triton X-100, 20 mM TriS, pH 8.0 to 1.0M NaCl in TriS/Triton as indicated in the tracing. Fractions were analyzed for arginine deiminase specific activity (hatched bars- =arginine deiminase specific activity (citrulline formation/mg protein), error bars shows standard error of triplicate samples), and by SDS-PAGE (FIG. 3). In FIG. 2, the dashed line indicates the salt gradient and the solid line indicates absorbance of column fractions at 280 nm.

FIG. 3 shows SDS-PAGE, 12.5% slab gels, analysis of HPLC fractions of M. orale proteinase K digest shown in FIG. 2. Lane M —$M_r$ markers. Lanes 1 to 24—HPLC fraction number correlating to fractions in FIG. 2.

EXAMPLE 2

Since artifacts were inherent in the methods used, including absorption from Hepes, CHAPS and phosphate buffer contaminants, and unprogrammed steep pH gradient generated from anion exchange of the buffer components themselves (as much as 3 pH units), a different purification scheme was followed.

Since it was demonstrated that detergents are not necessary for extraction, it was found that detergents could be successfully eliminated from anion exchange HPLC buffers. A change to the use of Tris buffers was also made. The use of Tris buffers, which are free of absorbing contaminant peaks and significant shifts in pH (only 0.2 pH units during the 0–1M NaCl gradient), enables increased sensitivity by monitoring at 254 nm. Such fractionations can be done on semipreparation anion exchange columns with 16-fold increased capacity.

Figure 4:
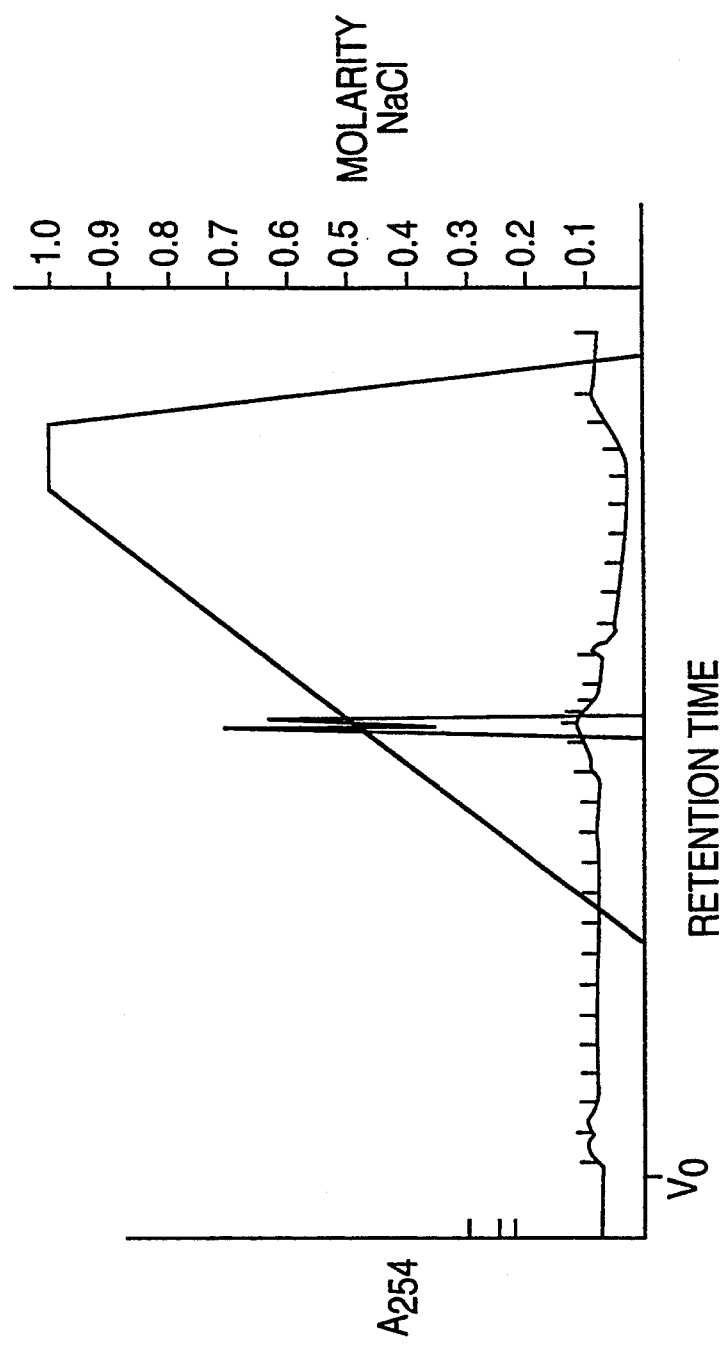

FIG. 4 shows the fractionation of proteinase K digested extracts of M. arginini on a semi-preparative (7.5×150 mm) Waters' DEAE 5PW anion-exchange column in the absence of detergent. Samples were fractionated with a 30-minute linear gradient of 0.02M Tris, pH 7.9 to 1M NaCl in Tris. Fractions were analyzed for arginine by citrulline formation and SDS-PAGE. The arginine deiminase peaks are shaded.

EXAMPLE 3

Various mycoplasma species were extracted with detergent or water and digested with proteinase K followed by HPLC purification.

Proteinase K-resistant arginine deiminase from two species, M. arginini and M. orale, were purified and characterized. Proteinase K resistant arginine deiminase was also identified in a third species, M. salivarium. The proteinase K-resistant form of the enzyme was found to be absent in two species, M. fermentans and Acholeplasma laidlawii. Proteinase K resistant proteins were found to be absent from M. pneumoniade, a species which does not hydrolyze arginine ior energy.

Figure 5:
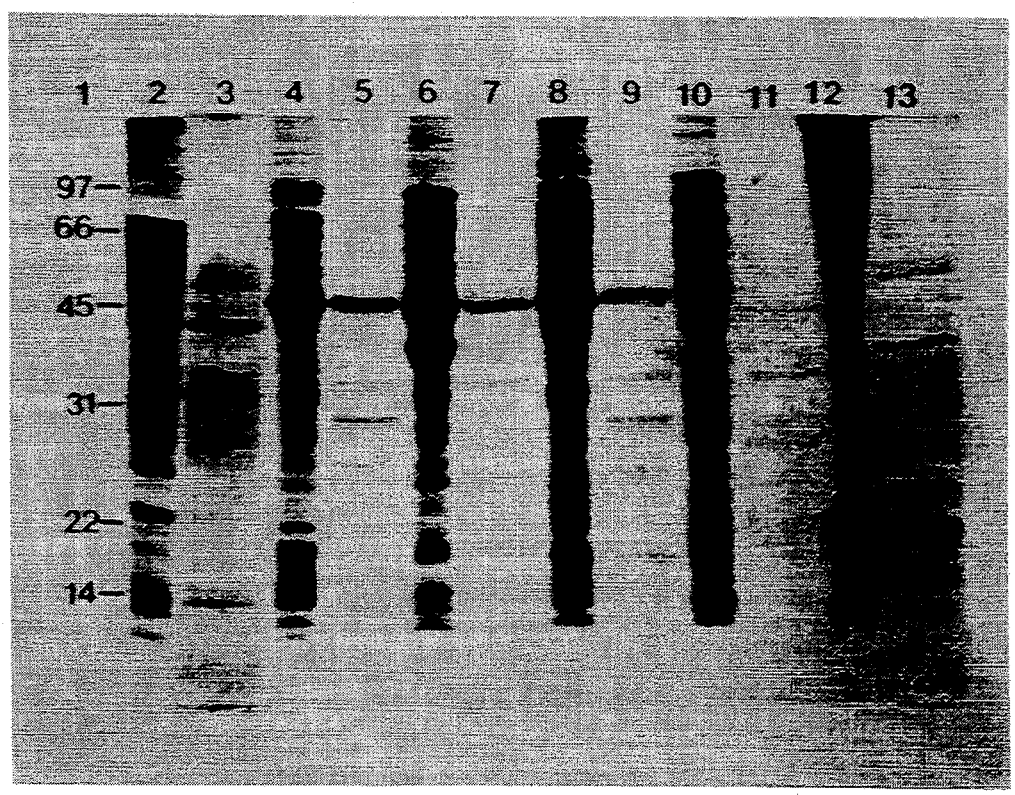
FIG. 5 shows the purification of proteinase K resistant arginine deiminase in various mycoplasma species.

FIG. 5 shows SDS-PAGE of CHAPS extracts (even numbered lanes) and proteinase K digests (100 μg proteinase K/ml for 24 hours) of extracts (odd numbered lanes) of the tested organisms. Lane 1—$M_r$ markers. Lanes 2 and 3—M. pneumoniae. Lanes 4 and 5—M. orale. Lanes 6 and 7—M. arginini. Lanes 8 and 9—M. salivarium. Lanes 10 and 11—M. fermentans. Lanes 12 and 13—A. laidlawii.

From FIG. 5 it is seen that proteinase K resistant 46,000 $M_r$ proteins (arginine deiminase) were detected in some arginine hydrolyzing species (M. orale, M. salivarium and M. arginini) but not in others (M. fermentans and A. laidlawii) and that proteinase K resistant proteins were not seen in M. pneumoniae.

The proteinase K digested fractions have been shown to be free (<1 endotoxin unit (EU)/ml) of endotoxin by the Limulus Amoebocyte Lysate (LAL) test.

The purified proteinase K resistant arginine deiminase of the invention have been shown to inhibit the growth of tumor cells as illustrated in Examples 4 and 5.

EXAMPLE 4

The proteinase K resistant arginine deiminases of M. arginine and M. orale have been shown to be effective in vitro against MOLT-4 human T cell leukemia cells at doses of 20 ng/ml, $10^3$ lower than the in vitro tumor toxic doses of mammalian arginases for several tumor cell lines (Bach et al. (1965) Br. J. Ca. 19:379–384), and eight-fold lower than that (166 ng/ml) which was toxic for normal primary mouse splenocyte cultures. Twenty ng/ml was the lowest dose tested. Miyazaki et al. (Cancer Research (1990) 50:4522–4527) reported approximately 50% killing at 5 ng/ml. Thus, the minimal effective in vitro dose remains to be determined.

Figure 6:
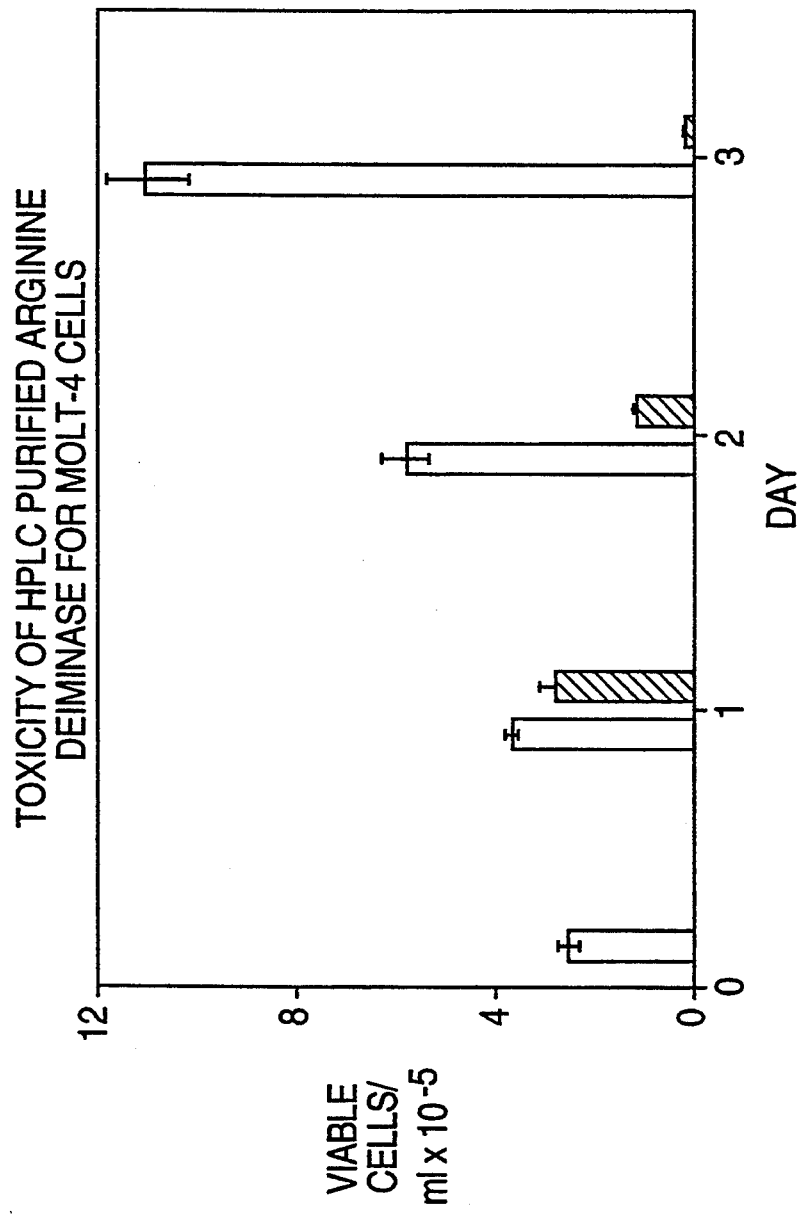
FIG. 6 shows the in vitro toxicity of *M. orale* HPLC-purified proteinase K resistant arginine deiminase for human MOLT-4 T cell leukemia line.

FIG. 6 shows the in vitro toxicity of M. orale and M. arginini HPLC-purified proteinase K resistant arginine deaminases for human MOLT-4 T cell leukemia line. 2.5×$10^5$ MOLT-4 cells/ml were cultured in the presence (filled bars) or absence (open bars) of 20 ng/ml M. oral arginine deiminase. Identical day 4 data was obtained for the M. arginini enzyme. Viable cell concentration ±SEM (n=3) were determined daily by trypan blue exclusion.

EXAMPLE 5

$10^5$/ml MOLT-4 cells, L1210 cells or P388D1 cells were incubated for 4 days in 0 to 1280 ng/ml M. arginini arginine deiminase. MOLT-4 cells were grown in 90% RPMI-1640, 10% FBS. L1210 and P388D1 cells were grown in 90% Fisher's medium, 10% horse serum. An in vitro MTT cytotoxicity assay (Denizot et al. (1986) J. Immunoo Meth. 89:271–277) was established wherein the correlation of formazan production ($A_{560}$–$A_{690}$) to viable cell number was determined for each cell line by a standard curve. Arginine deiminase induced tumor toxicity was determined as reduced formazan production (viable cell concentration) relative to untreated controls.

Figure 7:
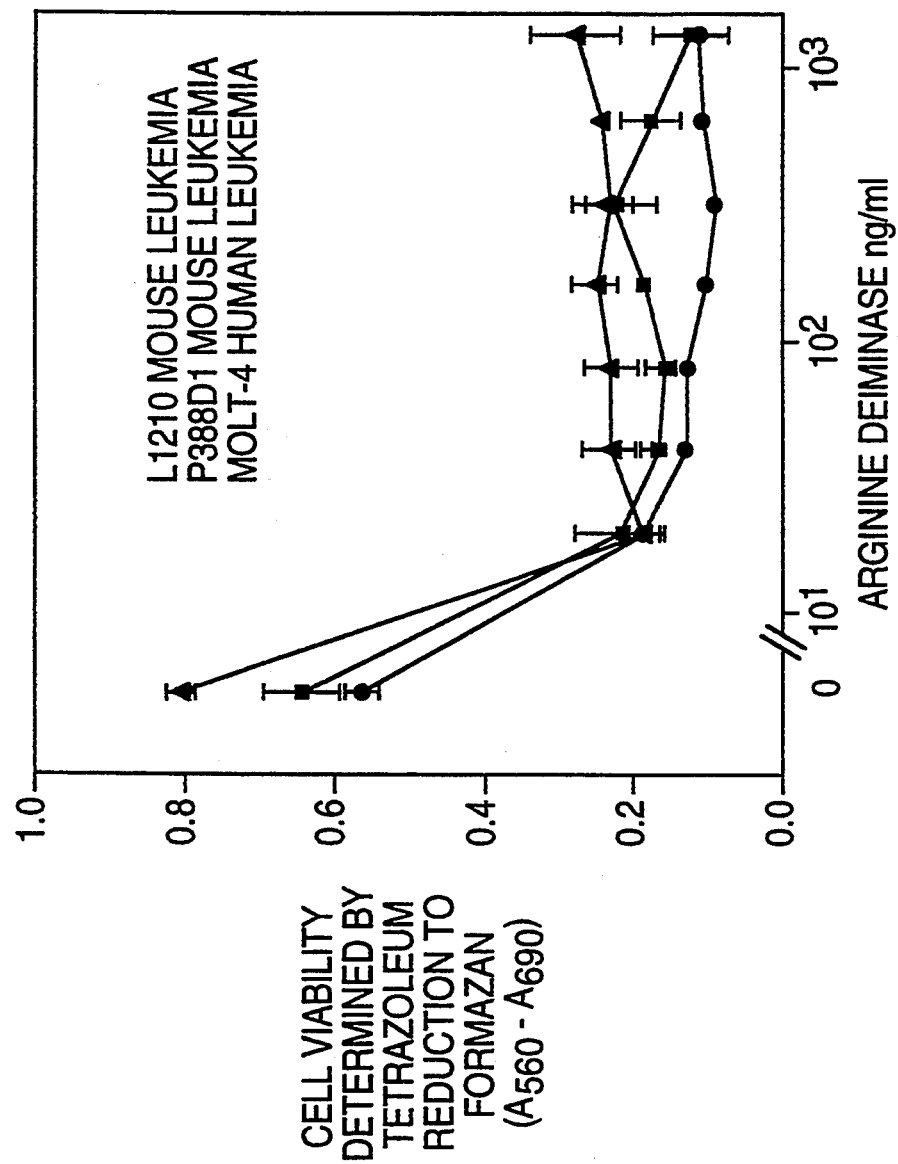
FIG. 7 shows the in vitro toxicity of *M. arginini* arginine deiminase for MOLT-4 and mouse leukemia cell lines L1210 and P388D1.
Figure 8:
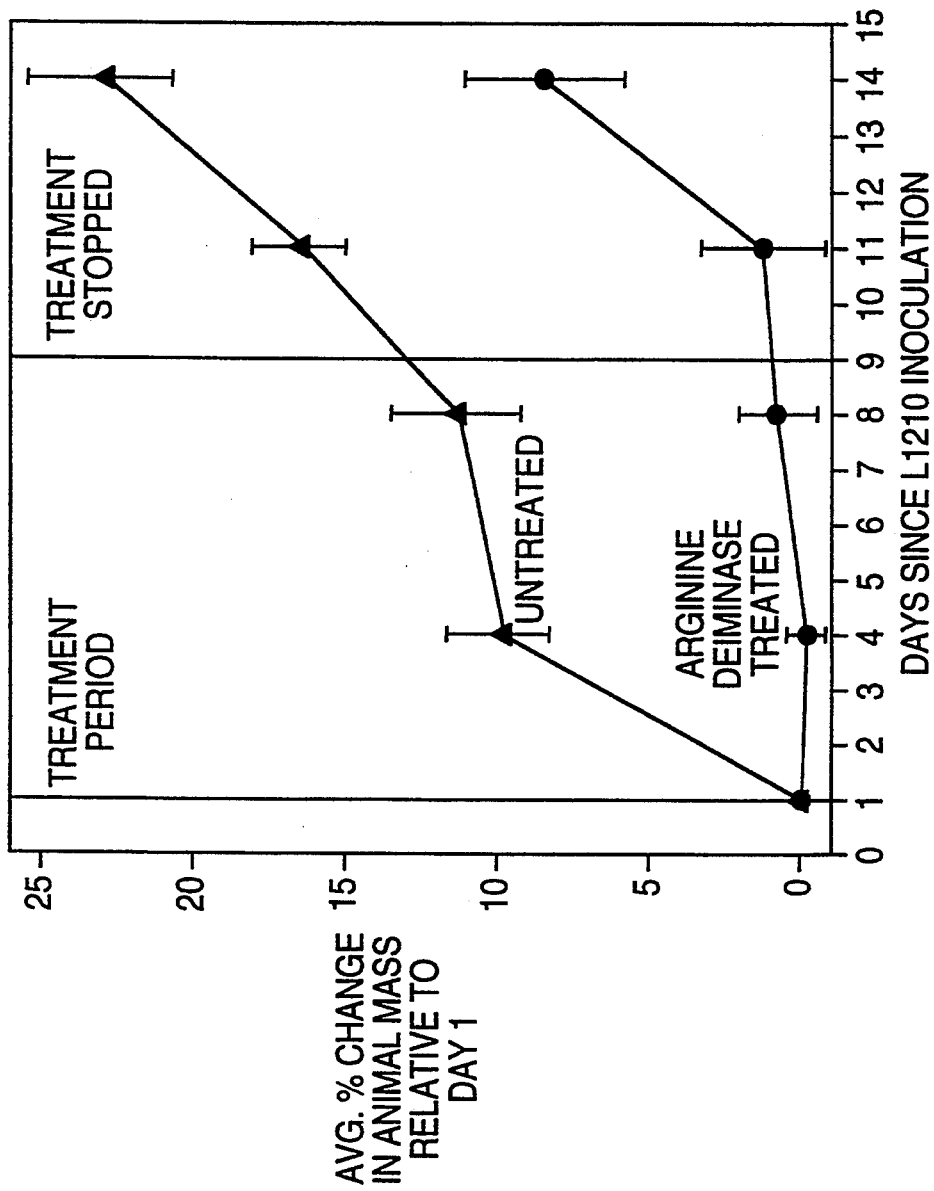
FIG. 8 shows the in vivo effect of arginine deiminase on L1210 tumor progression in nude mice.

FIG. 7 shows that L1210 (squares) and P388D1 (triangles) mouse leukemias as well as the MOLT-4 human leukemia (circles) are sensitive to 20 ng/ml of arginine deiminase. Arginine deiminase yields 100% cytotoxicity of 20 ng/ml for all three cell lines.

A human monocyte cell line, U937, was not affected by 20 or 50 ng/ml of arginine deiminase.

EXAMPLE 6

Ten nude mice were intraperitoneally (i.p.) inoculated with $10^5$ L1210 cells on day 0. Six of the mice were treated with 18.3 µg arginine deiminase, i.p., on days 1–9. Four of the mice were given PBS, i.p., as untreated controls.

Animals were weighed on days 1, 4, 8, 11 and 14 to monitor tumor progression and drug-toxicity. None of the treated animals lost weight relative to the untreated control animals. At day 9, when treatment was stopped, 5 of 6 treated mice had no significant weight gain, 1 of 6 gained 1.2 gm. The average weight gain was less than 1%. Average weight gain increased to 8.6% by day 14, one week after treatment stopped. L1210 tumors progressed rapidly in all untreated mice, with an average weight gain of 11.5% on day 9 and 23% by day 14. The T/C based on tumor progression was 1.83. Mortality was also decreased in the treated group.

Table 1 shows the effect of arginine deiminase treatment in L1210 tumor progression in nude mice. This date shown that arginine deiminase inhibits tumor progression in vivo.

life of the compound by a factor of 4 (Sovoca et (1984) Ca. Biochem. Biophys. 7:261–268).

Example 7 illustrates how arginine deiminase is modified by covalently linking PEG to the purified proteinase K resistant arginine deiminase of the invention.

EXAMPLE 7

Cyanuric chloride-activated PEG-1000 is added in tenfold molar excess to proteinase K resistant arginase deiminase in 0.1M sodium tetraborate, pH 9.2, and maintained at pH 9.2 with continuous stirring for one hour at 4° C. Unbound PEG-1000 is removed by ultrafiltration in an Amicon 8010 concentrator with a 30 kDa cutoff PM30 membrane. Reduction in immunogenicity is measured by immunizing 6 BALB/c mice each with subcutaneous doses of 100 µg PEG-modified or non-modified proteinase K resistant arginine deiminase in complete Freund's adjuvant weekly for 4 weeks. Blood is drawn from the tail vein after an additional week, and antibodies to arginine deiminase and PEG-modified arginine deiminase quantitated by immuno-dot-blotting using filtered antigen and perioxidase-conjugated antiglobulin.

We claim:

1. A method of purifying arginine deiminase comprising:
   extracting from a cell culture a mycoplasmal arginine deiminase obtained from a mycoplasma species which uses arginine as an energy source;
   digesting the extract with proteinase K at a buffer concentration of at least about 0.1N; and
   obtaining purified arginine deiminase from said proteinase K-digested extract.

2. The method of claim 1, wherein the proteinase K-treated extract is further purified by filtering said proteinase K-treated extract and subjecting the filtrate to high pressure liquid chromatography.

3. The method of claim 1 wherein said arginase deimi-

TABLE 1

| Animal # | Animal Mass (Gm) | | | | | | Mortality | | | |
|---|---|---|---|---|---|---|---|---|---|---|
| | Day 1 | Day 4 | Day 8 | Day 9 | Day 11 | Day 14 | Day 20 | Day 21 | Day 22 | Day 23 |
| Arginine Deiminase Treated | | | | | | | | | | |
| E1 | 33.85 | 33.67 | 33.99 | | 33.95 | 35.58 | | | Dead | |
| E2 | 34.21 | 34.15 | 34.42 | | 34.36 | 37.16 | | Dead | | |
| E3 | 36.19 | 36.13 | 36.54 | | 36.8 | 36.36 | | Dead | | |
| E4 | 31.81 | 31.76 | 31.85 | | 32.4 | 35.39 | Dead | | | |
| E5 | 34.8 | 35.72 | 36 | | 36.49 | 37.41 | | | | Dead |
| E6 | 31.66 | 30.79 | 31.7 | | 31.2 | 35.53 | | Dead | | |
| Average % Change vs Day 1: | | −0.19% | +0.91% | | +1.37% | +8.59% | | | | |
| Untreated Control | | | | | | | | | | |
| C1 | 31.79 | 34.68 | 35.58 | | 37.23 | 37.44 | | Dead | | |
| C2 | 33.9 | 37.99 | 38.84 | | 40.59 | 41.06 | Dead | | | |
| C3 | 31.07 | 32.8 | 32.74 | | 35 | 38.83 | | Dead | | |
| C4 | 30.2 | 34.2 | 34.5 | | 35.47 | 38.96 | | Dead | | |
| Average % Change vs Day 1: | | +9.99% | +11.5% | | +16.74% | +23.22% | | | | |

An anticipated adverse effect of using a proteinaceous agent as a therapeutic agent is the host immune response to the agent. Reduction of immunogenicity of enzymes using PEG can be accomplished without acceptable losses of activity.

L-asparaginases, which are currently used as antineoplastic agents, have been PEG-modified with 50% loss of specific activity, but with significant loss of immunogenicity. The use of PEG-conjugates of L-asparaginase resulted in an extension of the circulating halfnase is extracted by sonification in water.

4. The method of claim 1, wherein said mycoplasma species is *M. arginini* or *M. orale*.

5. The method of claim 1 wherein the arginine deiminase is extracted with detergent or water.

6. The method of claim 5 wherein the arginine deiminase is extracted with water.

7. The method of claim 6 wherein purified arginine deiminase is obtained by filtering the proteinase K digested extract and subjecting the tiltrate to high pressure liquid chromatography.

* * * * *